US010380786B2

(12) United States Patent
Steen (10) Patent No.: US 10,380,786 B2
(45) Date of Patent: Aug. 13, 2019

(54) METHOD AND SYSTEMS FOR SHADING AND SHADOWING VOLUME-RENDERED IMAGES BASED ON A VIEWING DIRECTION (71) Applicant: General Electric Company, Schenectady, NY (US)

(72) Inventor: Erik Normann Steen, Moss (NO)

(73) Assignee: General Electric Company, Schenectady, NY (US)

( * ) Notice: Subject to any disclaimer, the term of this patent is extended or adjusted under 35 U.S.C. 154(b) by 1111 days.

(21) Appl. No.: 14/726,369

(22) Filed: May 29, 2015

(65) Prior Publication Data
US 2016/0350962 A1 Dec. 1, 2016

(51) Int. Cl.
*A61B 8/08* (2006.01)
*G06T 15/08* (2011.01)
*G06T 15/60* (2006.01)
*G06T 15/80* (2011.01)

(52) U.S. Cl.
CPC ............ *G06T 15/08* (2013.01); *G06T 15/60* (2013.01); *G06T 15/80* (2013.01); *A61B 8/483* (2013.01); *G06T 2210/41* (2013.01)

(58) Field of Classification Search
CPC ......... G06T 15/08; G06T 15/80; G06T 15/60; G06T 2210/41; A61B 8/483
See application file for complete search history.

(56) References Cited

U.S. PATENT DOCUMENTS

| | | | | |
|---|---|---|---|---|
| 4,984,157 A | * | 1/1991 | Cline | G06T 15/08 345/424 |
| 6,724,383 B1 | * | 4/2004 | Herken | G06T 15/80 345/420 |
| 2004/0169652 A1 | * | 9/2004 | Herken | G06T 15/80 345/426 |
| 2005/0043619 A1 | * | 2/2005 | Sumanaweera | G06T 15/08 600/437 |
| 2007/0002047 A1 | | 1/2007 | Desgranges et al. | |
| 2012/0269416 A1 | * | 10/2012 | Waki | A61B 8/08 382/131 |
| 2013/0150719 A1 | | 6/2013 | Orderud | |
| 2013/0169641 A1 | | 7/2013 | Schroecker | |
| 2014/0184600 A1 | * | 7/2014 | Steen | G06T 15/08 345/424 |

OTHER PUBLICATIONS

Engel, K. et al., "Real-Time Volume Graphics, Chapter 6.1: Global Volume Illumination," Jul. 21, 2006, A K Peters/CRC Press, 11 pages.
Schroecker, Gerald, "Method, System, and Medical Imaging Device for Shading Volume-Rendered Images with Multiple Light Sources," U.S. Appl. No. 14/468,742, filed Aug. 26, 2014, 34 pages.
Schroecker, Gerald, "Method and Apparatus for Rendering an Ultrasound Image," U.S. Appl. No. 14/549,768, filed Nov. 21, 2014, 20 pages.

* cited by examiner

Primary Examiner — Peter Luong
(74) Attorney, Agent, or Firm — McCoy Russell LLP (57) ABSTRACT Various methods and systems are provided for generating a volume-rendered image with shading from a three-dimensional ultrasound dataset. As one example, a method for ultrasound imaging includes generating a volume-rendered image with shading and shadowing from a three-dimensional ultrasound dataset, the shading and shadowing based on an angle between a probe axis of a transducer probe used to acquire the three-dimensional ultrasound dataset and a viewing direction of the volume-rendered image.

20 Claims, 4 Drawing Sheets

METHOD AND SYSTEMS FOR SHADING AND SHADOWING VOLUME-RENDERED IMAGES BASED ON A VIEWING DIRECTION

FIELD

Embodiments of the subject matter disclosed herein relate to methods and systems for shading and shadowing volume-rendered images.

BACKGROUND

Volume-rendered images may be useful for representing 3D medical imaging datasets. There are currently many different techniques for generating a volume-rendered image. One such technique, ray-casting, includes traversing a number of rays through the 3D medical imaging dataset. Each volume sample (e.g., voxel) encountered during ray casting is mapped to a color and a transparency value. According to one approach, the color and opacity values are accumulated along each ray using front-to-back or back-to-front volume composition and the accumulated color value is displayed as a pixel in the volume-rendered image. In order to gain an additional sense of the orientation of surfaces within the volumetric data, volume-rendered images may be shaded using gradient shading techniques. Gradient shading techniques compute reflections based on implicitly defined surface normals computed from volume gradients relative to a pre-defined light direction. Both diffuse and specular reflections are taken into account in the gradient shaded volume-rendered image. Other shading methods, such as methods based on computing gradients from a depth buffer may be used instead of gradient shading. Furthermore, volumetric shadowing techniques can be used to enhance perception of depth as well as shapes of structures within the volumetric data. Volumetric shadowing techniques take a predefined light direction or pre-defined light source position into account for computing the shadows. Various methods for shading and volumetric shadowing (hereafter simply referred to as shadowing) are known to those skilled in the art. The shading and shadowing help a viewer to more easily visualize the three-dimensional shape of the object represented by the volume-rendered image.

Some ultrasound imaging systems typically allow the user to control rotation of the volume-rendered image in order to change a viewing direction of the image. However, the resolution of the volume-rendered image may be anisotropic, for example, when the ultrasound image is acquired at fundamental frequencies. As such, the image resolution changes from a radial direction (e.g., a direction normal to the transducer probe surface and in a direction of a probe axis of the transducer probe) to a lateral (e.g., a direction perpendicular to the transducer probe surface normal, also referred to herein as a side view) and elevation direction. For example, when ultrasound data is viewed from the lateral direction, the resulting volume-rendered image has a more noisy and unstable appearance than when the ultrasound data is viewed from the radial direction. Many of the shadows and reflections created in the lateral view volume-rendered image may not correspond to real structures, thereby degrading the ability of the user to make an accurate medical diagnosis. These issues have been recognized by the inventors herein, and are not admitted to be generally known.

BRIEF DESCRIPTION

In one embodiment, a method for ultrasound imaging comprises generating a volume-rendered image with shading and shadowing from a three-dimensional ultrasound dataset, the shading and shadowing based on an angle between a probe axis of a transducer probe used to acquire the three-dimensional ultrasound dataset and a viewing direction of the volume-rendered image.

It should be understood that the brief description above is provided to introduce in simplified form a selection of concepts that are further described in the detailed description. It is not meant to identify key or essential features of the claimed subject matter, the scope of which is defined uniquely by the claims that follow the detailed description. Furthermore, the claimed subject matter is not limited to implementations that solve any disadvantages noted above or in any part of this disclosure.

BRIEF DESCRIPTION OF THE DRAWINGS

The present invention will be better understood from reading the following description of non-limiting embodiments, with reference to the attached drawings, wherein below.

DETAILED DESCRIPTION

The following description relates to various embodiments of generating a volume-rendering image with viewing angle-dependent shading and shadowing. An ultrasound imaging system, such as the system shown in FIG. 1 may be used to acquire three-dimensional ultrasound data via a transducer probe. A processor of the ultrasound imaging system may access the three-dimensional ultrasound data and use various techniques, such as the example technique depicted in FIG. 2, to generate a volume-rendered image from the three-dimensional ultrasound data. Shading and shadowing may be used to enhance the volume rendered image. For example, shading and shadowing may be determined based on one or more shading and shadowing parameters such as a light source position, light source strength, and light attenuation. However, due to the nature of the ultrasound data (e.g., due to the anisotropic nature of the ultrasound imaging system), the volume resolution of the volume-rendered image is anisotropic. Thus, when the volume-rendered image is viewed from different viewing directions relative to a probe axis of the transducer probe, as shown in FIG. 3, the appearance of the rendered image changes. For example, as an angle between the probe axis and the viewing direction increases, the rendered image may become degraded. Thus, a method, such as the method shown in FIG. 4, may include adjusting the one or more volume-rendering shading and shadowing parameters based on the angle between the probe axis and the viewing direction.

Figure 1:
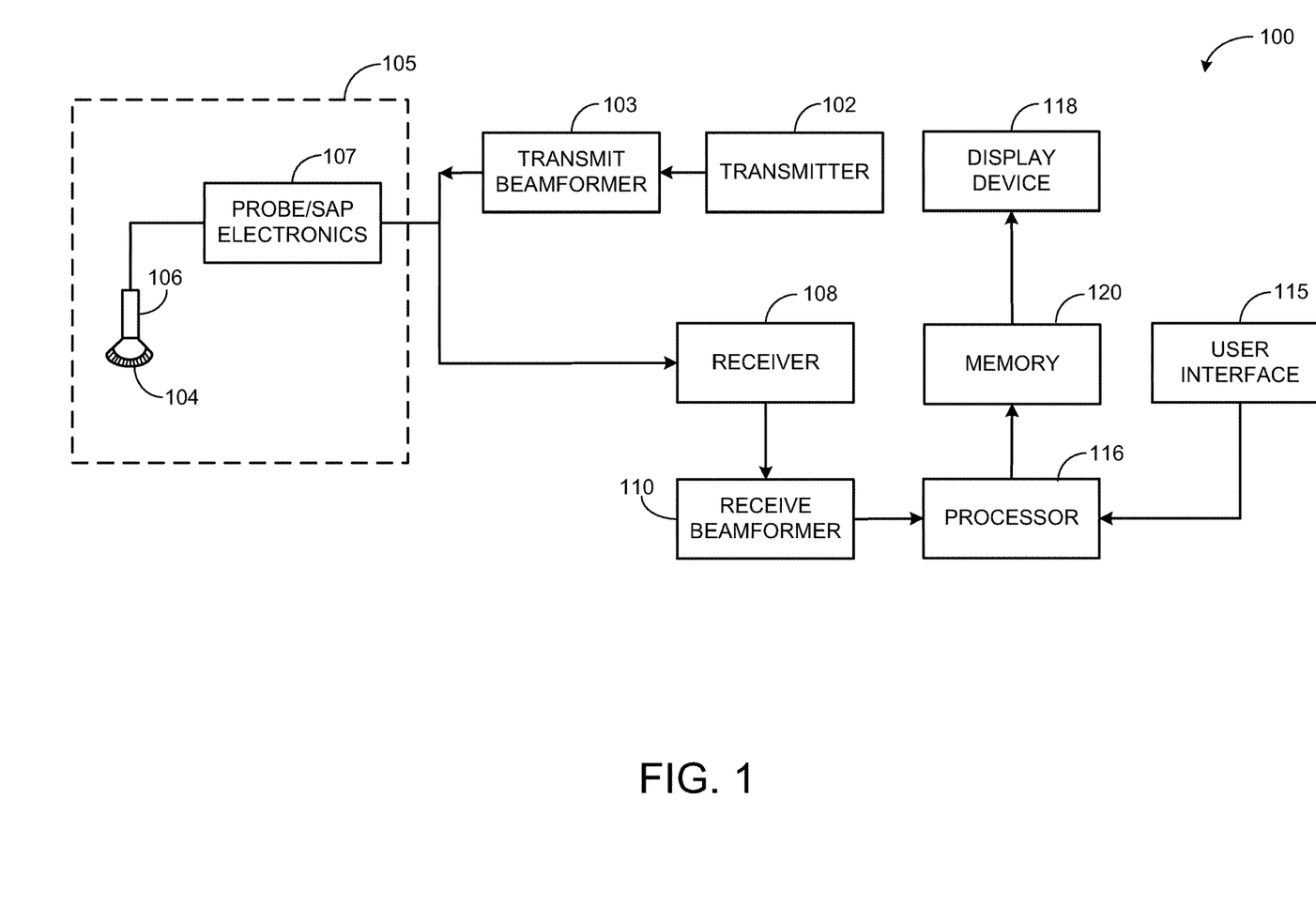
FIG. 1 is a schematic diagram of an ultrasound imaging system according to an embodiment.

Before further discussion of the approach for generating the volume-rendered image with viewing angle dependent shading and shadowing, an example ultrasound imaging system that may be used to acquire three-dimensional ultrasound data is shown in FIG. 1. Specifically, FIG. 1 is a schematic diagram of an ultrasound imaging system 100 in accordance with an embodiment. The ultrasound imaging system 100 includes a transmitter 102 that transmits a signal to a transmit beam former 103 which in turn drives transducer elements 104 within a transducer array 106 to emit pulsed ultrasonic signals into a structure, such as a patient (not shown). A probe 105 includes the transducer array 106, the transducer elements 104 and probe/SAP electronics 107. The probe 105 may be an electronic 4D (E4D) probe, a mechanical 3D probe, or any other type of probe capable of acquiring three-dimensional ultrasound data. The probe/SAP electronics 107 may be used to control the switching of the transducer elements 104. The probe/SAP electronics 107 may also be used to group the transducer elements 104 into one or more sub-apertures. A variety of geometries of transducer arrays may be used. The pulsed ultrasonic signals are back-scattered from structures in the body, like blood cells or muscular tissue, to produce echoes that return to the transducer elements 104. The echoes are converted into electrical signals, or ultrasound data, by the transducer elements 104 and the electrical signals are received by a receiver 108. The electrical signals representing the received echoes are passed through a receive beam-former 110 that outputs ultrasound data or three-dimensional ultrasound data. A user interface 115 may be used to control operation of the ultrasound imaging system 100, including, to control the input of patient data, to change a scanning or display parameter, and the like.

The ultrasound imaging system 100 also includes a processor 116 to process the ultrasound data and generate frames or images for display on a display device 118. The processor 116 may include one or more separate processing components. For example, the processor 116 may include a central processing unit (CPU), a microprocessor, a graphics processing unit (GPU), or any other electronic component capable of processing inputted data according to specific logical instructions. Having a processor that includes a GPU may advantageous for computation-intensive operations, such as volume-rendering, which will be described in more detail hereinafter. The processor 116 is in electronic communication with the probe 105, the display device 118, and the user interface 115. The processor 116 may be hard-wired to the probe 105 and the display device 118, and the user interface 115, or the processor 116 may be in electronic communication through other techniques including wireless communication. The display device 118 may be a flat panel LED display according to an embodiment. The display device 118 may include a screen, a monitor, a projector, a flat panel LED, or a flat panel LCD according to other embodiments.

The processor 116 may be adapted to perform one or more processing operations according to a plurality of selectable ultrasound modalities on the ultrasound data. Other embodiments may use multiple processors to perform various processing tasks. The processor 116 may also be adapted to control the acquisition of ultrasound data with the probe 105. The ultrasound data may be processed in real-time during a scanning session as the echo signals are received. For purposes of this disclosure, the term "real-time" is defined to include a process performed with no intentional lag or delay. An embodiment may update the displayed ultrasound image at a rate of more than 20 times per second. The images may be displayed as part of a live image. For purposes of this disclosure, the term "live image" is defined to include a dynamic image that is updated as additional frames of ultrasound data are acquired. For example, ultrasound data may be acquired even as images are being generated based on previously acquired data and while a live image is being displayed. Then, according to an embodiment, as additional ultrasound data are acquired, additional frames or images generated from more-recently acquired ultrasound data are sequentially displayed. Additionally or alternatively, the ultrasound data may be stored temporarily in a buffer during a scanning session and processed in less than real-time in a live or off-line operation. Other embodiments of the invention may include multiple processors (not shown) to handle the processing tasks. For example, a first processor may be utilized to demodulate and decimate the ultrasound signal while a second processor may be used to further process the data prior to displaying an image. It should be appreciated that other embodiments may use a different arrangement of processors.

The processor 116 may be used to generate an image, such as a volume-rendered image or a planar image, from a three-dimensional ultrasound data acquired by the probe 105. According to an embodiment, the three-dimensional ultrasound data includes a plurality of voxels, or volume elements. Each of the voxels is assigned a value or intensity based on the acoustic properties of the tissue corresponding to a particular voxel.

Still referring to FIG. 1, the ultrasound imaging system 100 may continuously acquire ultrasound data at a frame rate of, for example, 5 Hz to 50 Hz depending on the size and spatial resolution of the ultrasound data. However, other embodiments may acquire ultrasound data at a different rate. A memory 120 is included for storing processed frames of acquired ultrasound data that are not scheduled to be displayed immediately. The frames of ultrasound data are stored in a manner to facilitate retrieval thereof according to the order or time of acquisition. As described hereinabove, the ultrasound data may be retrieved during the generation and display of a live image. The memory 120 may include any known data storage medium for storing data, including, but not limited to a hard drive, a flash memory, random access memory (RAM), read only memory (ROM), a compact disc (CD), and a compact disc read-only memory (CD-ROM). The memory 120 may be part of a database, a component of a PACS/RIS system, or a stand-alone component. The processor 116 is communicatively connected to the memory 120. This may be via either a wired or a wireless connection.

Optionally, embodiments of the present invention may be implemented utilizing contrast agents. Contrast imaging generates enhanced images of anatomical structures and blood flow in a body when using ultrasound contrast agents including microbubbles. After acquiring ultrasound data while using a contrast agent, the image analysis includes separating harmonic and linear components, enhancing the harmonic component and generating an ultrasound image by utilizing the enhanced harmonic component. Separation of harmonic components from the received signals is performed using suitable filters. The use of contrast agents for ultrasound imaging is well known by those skilled in the art and will therefore not be described in further detail.

In various embodiments of the present invention, ultrasound data may be processed by other or different mode-related modules. The images are stored and timing information indicating a time at which the image was acquired in memory may be recorded with each image. The modules may include, for example, a scan conversion module to perform scan conversion operations to convert the image frames from Polar to Cartesian coordinates. A video processor module may be provided that reads the images from a memory and displays the image in real time while a procedure is being carried out on a patient. A video processor module may store the image in an image memory, from which the images are read and displayed. The ultrasound imaging system 100 shown may be a console system, a cart-based system, or a portable system, such as a hand-held or laptop-style system according to various embodiments.

Figure 2:
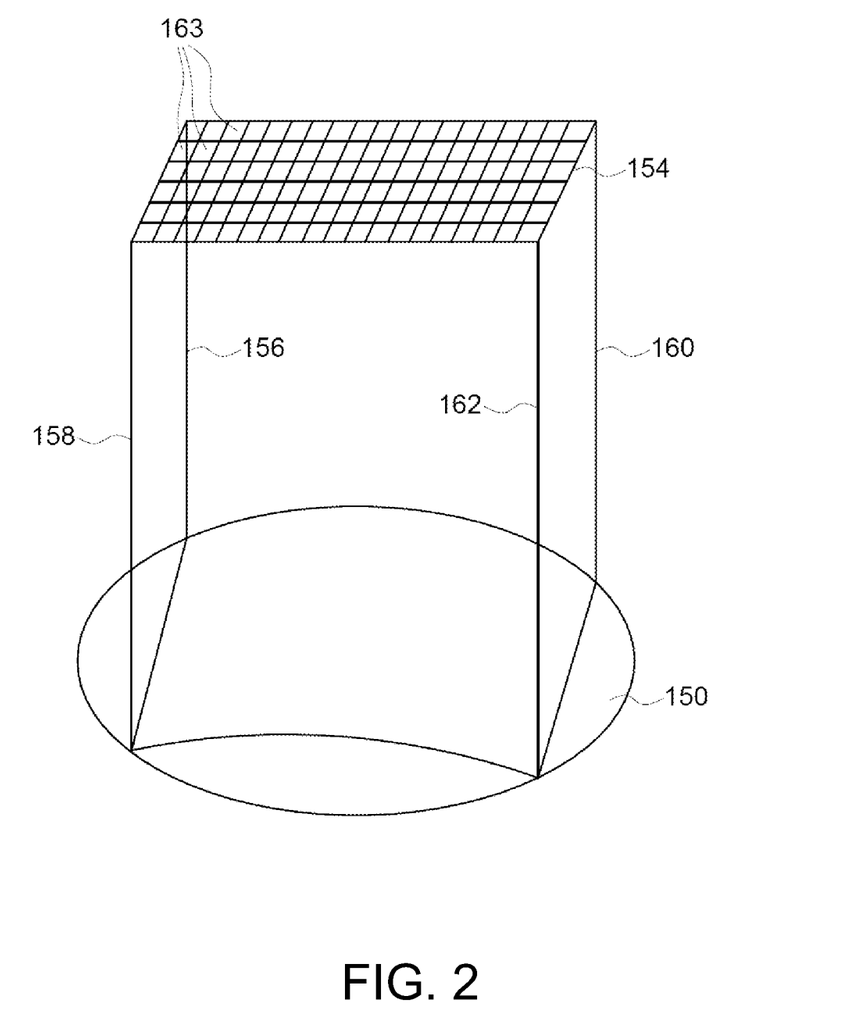
FIG. 2 is a schematic representation of a geometry that may be used to generate a volume-rendered image according to an embodiment.
Figure 3:
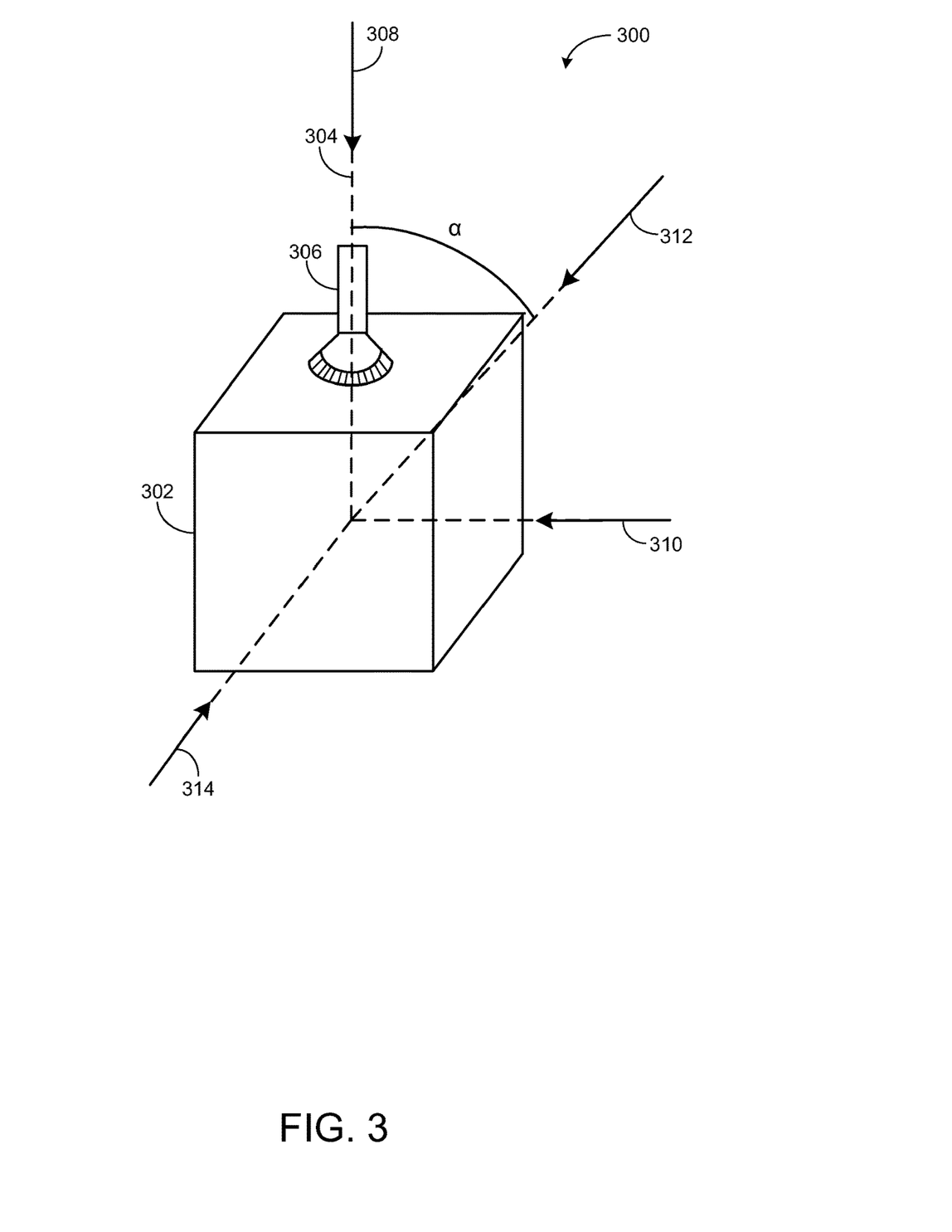
FIG. 3 is a schematic representation of different viewing directions of a volume-rendered image according to an embodiment.

FIG. 2 is a schematic representation of geometry that may be used to generate a volume-rendered image according to an embodiment. FIG. 2 includes a 3D medical imaging dataset 150 and a view plane 154.

Referring to both FIGS. 1 and 2, the processor 116 may generate a volume-rendered image according to a number of different techniques. According to an exemplary embodiment, the processor 116 may generate a volume-rendered image through a ray-casting technique from the view plane 154. The processor 116 may cast a plurality of parallel rays from the view plane 154 through the 3D medical imaging dataset 150. FIG. 2 shows a first ray 156, a second ray 158, a third ray 160, and a fourth ray 162 bounding the view plane 154. It should be appreciated that additional rays may be cast in order to assign values to all of the pixels 163 within the view plane 154. The 3D medical imaging dataset 150 may comprise voxel data, where each voxel, or volume-element, is assigned a value or intensity. Additionally, each voxel may be assigned an opacity as well. The value or intensity may be mapped to a color according to some embodiments. The processor 116 may use a "front-to-back" or a "back-to-front" technique for volume composition in order to assign a value to each pixel in the view plane 154 that is intersected by the ray. For example, starting at the front, that is the direction from which the image is viewed, the intensities of all the voxels along the corresponding ray may be summed. An opacity value, which corresponds to light attenuation, is assigned to each voxel. The intensity is multiplied by the opacity of the voxels along the ray to generate an opacity-weighted value. These opacity-weighted values are then accumulated in a front-to-back or in a back-to-front direction along each of the rays. The process of accumulating values is repeated for each of the pixels 163 in the view plane 154 in order to generate a volume-rendered image. According to an embodiment, the pixel values from the view plane 154 may be displayed as the volume-rendered image. The volume-rendering algorithm may additionally be configured to use an opacity function providing a gradual transition from opacities of zero (completely transparent) to 1.0 (completely opaque). The volume-rendering algorithm may account for the opacities of the voxels along each of the rays when assigning a value to each of the pixels 163 in the view plane 154. For example, voxels with opacities close to 1.0 will block most of the contributions from voxels further along the ray, while voxels with opacities closer to zero will allow most of the contributions from voxels further along the ray. Additionally, when visualizing a surface, a thresholding operation may be performed where the opacities of voxels are reassigned based on the values. According to an exemplary thresholding operation, the opacities of voxels with values above the threshold may be set to 1.0 while voxels with the opacities of voxels with values below the threshold may be set to zero. Other types of thresholding schemes may also be used. An opacity function may be used to assign opacities other than zero and 1.0 to the voxels with values that are close to the threshold in a transition zone. This transition zone may be used to reduce artifacts that may occur when using a simple binary thresholding algorithm. For example, a linear function mapping opacities to values may be used to assign opacities to voxels with values in the transition zone. Other types of functions that progress from zero to 1.0 may also be used. Volume-rendering techniques other than the ones described above may also be used in order to generate a volume-rendered image from a 3D medical imaging dataset.

The volume-rendered image may be shaded in order to present the user with a better perception of surface orientation. This may be performed in several different ways according to various embodiments. For example, a plurality of surfaces may be implicitly defined based on the volume-rendering of the 3D medical imaging dataset. According to an exemplary embodiment, a gradient may be calculated at each of the voxels. The processor 116 (shown in FIG. 1) may compute the amount of light at positions corresponding to each of the voxels and apply standard shading methods based on the gradients and specific light directions, as well as other parameters such as light strength, attenuation and reflectivity. The shading process may incorporate both specular and diffuse reflections to brighten image details. The specular and diffuse reflections simulate light reflections from the light source hitting the surfaces and bouncing back toward the viewer. Thus, the specular and diffuse reflections included in the volume rendering algorithm depend on the light direction, the local surface orientation (e.g., gradient normal), and the viewing direction used to create the volume-rendered image (the viewing direction will be described further below with reference to FIG. 3). In this way, the volume-rendered image may be shaded based on one or more volume-rendering shading parameters.

Generating the volume rendered image may further include applying shadowing effects to the image. Shadowing of volume rendered images may be performed according to different shadowing methods. Various types of lighting may be used in the shadowing process: direct lighting to create sharp shadows via monochromatic light attenuation, indirect lighting to create soft shadows via diffuse chromatic light attenuation, and/or ambient lighting to lighten dark portions of the image. The indirect lighting simulates light scattering effects, thereby creating soft colored shadows. Thus, in one example, the volume rendered image may include a combination of direct, indirect, and ambient lighting.

According to one exemplary embodiment, the 3D data set may be sliced with multiple planes orthogonal to half of an angle between the light direction and the viewing direction. Light intensity on each sliced plane is calculated based on the light intensity on a previous sliced plane and the opacity of each sample on the previous sliced plane. The calculated light intensity can then be applied to the voxels during volume composition for creating the shadowing effects. Thus, this exemplary method, or another possible shadowing method, may create one or more volume-rendering shadowing parameters for shadowing the volume-rendered image.

Further, as introduced above, the shadows and light reflections of the volume-rendered image may change based on a direction of the light source applied to the volume-rendered image.

The view direction may correspond with the view direction shown in FIG. 2. The processor 116 may also use multiple light sources as inputs when generating the volume-rendered image. For example, when ray casting, the processor 116 may calculate how much light is reflected, scattered, or transmitted from each voxel in a particular view direction along each ray. This may involve summing contributions from multiple light sources. The processor 116 may calculate the contributions from all the voxels in the volume. The processor 116 may then composite values from all of the voxels, or interpolated values from neighboring voxels, in order to compute the final value of the displayed pixel on the image. While the aforementioned example described an embodiment where the voxel values are integrated along rays, volume-rendered images may also be calculated according to other techniques such as using the highest value along each ray, using an average value along each ray, or using any other volume-rendering technique.

FIG. 3 is a schematic representation of a volume-rendered image and different viewing directions of the volume-rendered image relative to a probe axis. Specifically, schematic 300 of FIG. 3 shows a geometrical representation of a volume-rendered image 302 and the relative positioning of a probe axis 304 of a transducer probe 306 used to acquire the 3D ultrasound data represented by the volume-rendered image 302. As one example, as shown in FIG. 3, the probe axis 304 is the central axis of the transducer probe which is positioned normal to a plane tangent to a surface formed by the transducer elements of the transducer probe 304. Thus, in some examples, the probe axis 304 may also coincide with a transducer surface normal. FIG. 3 shows a positioning of the transducer probe 304 as used to acquire the 3D ultrasound data represented by the volume-rendered image.

Arrow 308 shows a radial direction which is defined as being parallel to the probe axis 304. For example, when the radial direction 308 is the viewing direction, the user may be presented with a top-down view of the scanned object represented by the volume-rendered image.

The resolution of some ultrasound data may be anisotropic in nature. For example, the point spread function of the ultrasound imaging system (e.g., such as the ultrasound imaging system 100 shown in FIG. 1) may be highly asymmetric and thus the resolution of the resulting volume-rendered image is different in the radial direction 308 versus a lateral direction (as show by arrow 310) and an elevation direction (as shown by arrow 314). More specifically, the image resolution in the radial direction 308 is higher than in the lateral direction 310 and the elevation direction 314. As shown in FIG. 3, the lateral direction 310 is perpendicular to the probe axis 304. Additionally, the elevation direction 314 is perpendicular to the probe axis 304 (and radial direction) and the lateral direction 310.

A user may adjust the viewing direction via a user interface (such as user interface 115 shown in FIG. 1) by rotating the volume-rendered image displayed on a display screen (such as display 118 shown in FIG. 1). As the viewing direction changes from the radial direction 308 and moves closer to the lateral direction 310, the resulting volume-rendered image may become increasingly noisy and/or unstable due to the anisotropic nature of the 3D ultrasound data. In some examples, the volume rendering parameters used in the volume rendering algorithm (e.g., including the volume-rendering shading parameters used to shade the image and volume-rendering shadowing parameters used to shadow the image), as described above, may result in different quality images for different viewing directions relative to a same probe axis. As one example, when a 3D dataset of a tissue is viewed from the side (e.g., lateral direction 310), the inherent speckle pattern in the data creates some shadows and reflections which do not correspond to real tissue structures. As such, medical diagnosis based on the resulting volume-rendered image may be less accurate.

Instead of applying the same shading and shadowing volume rendering parameters to all images, regardless of the viewing direction, at least during some selected conditions, a method may include adjusting the rendering parameters based on the viewing direction of the volume-rendered image relative to the probe axis 304. In other examples, the rendering may only be adjusted based on the viewing direction of the volume-rendered image relative to the probe axis during selected operating or viewing conditions, and in other conditions the rendering may be maintained independent of the viewing direction of the volume-rendered image relative to the probe axis 304. FIG. 3 shows an angle, a, defined between the transducer probe axis 304 of the transducer probe 306 and the viewing direction 312 of the volume-rendered image 302. A weighting function based on a may then be used to adjust the rendering parameters and therefore adjust the amount of opacity and light reflections represented in the volume-rendered image as a function of α. As one example, the weighting function is defined as:

$$1 - \sin(\alpha) * A \qquad \text{(equation 1)},$$

where A is an angle dependency term. As one example, the angle dependency term may be based on a known relationship between the viewing direction and an image quality of the volume-rendered image. As such, the angle dependency term may be different for different imaging systems and based on a point spread function of the imaging system (e.g., ultrasound imaging system). The output of the weighting function is then multiplied with the light reflection term (e.g., which may include a specular reflection term and/or a diffuse reflection term) as well as the light attenuation term (e.g., opacity) in the volume rendering algorithm. For example, when viewing the volume data from the transducer probe position (e.g., from the radial direction 308), sin(α)=0 and thus the weighting function is 1. As a result, the volume rendering shading and shadowing parameters (also referred to herein as shading and shadowing parameters), such as the light reflection term and the light attenuation term, are not adjusted and the volume-rendered image is shaded and shadowed according to the unadjusted parameters. However, as another example, when viewing the volume data from the side, or from the lateral direction 310, sin(α)=1 and thus the weighting function is 1−A. As a result, the volume rendering parameters are adjusted by 1−A and the resulting volume-rendered image is shaded and shadowed according to the adjusted rendering parameters. In this way, the shading and shadowing of the volume-rendered image may be adjusted based on the viewing angle relative to the transducer probe axis. By adjusting the shading and shadowing based on the angle α, the resolution of the volume-rendered image is made more isotropic than if the shading was not adjusted based on the angle α. Thus, adjusting the shading and shadowing based on the angle α produces more realistic volume-rendered images from any viewing angle and results in more accurate medical diagnosis from the angle-adjusted images.

Figure 4:
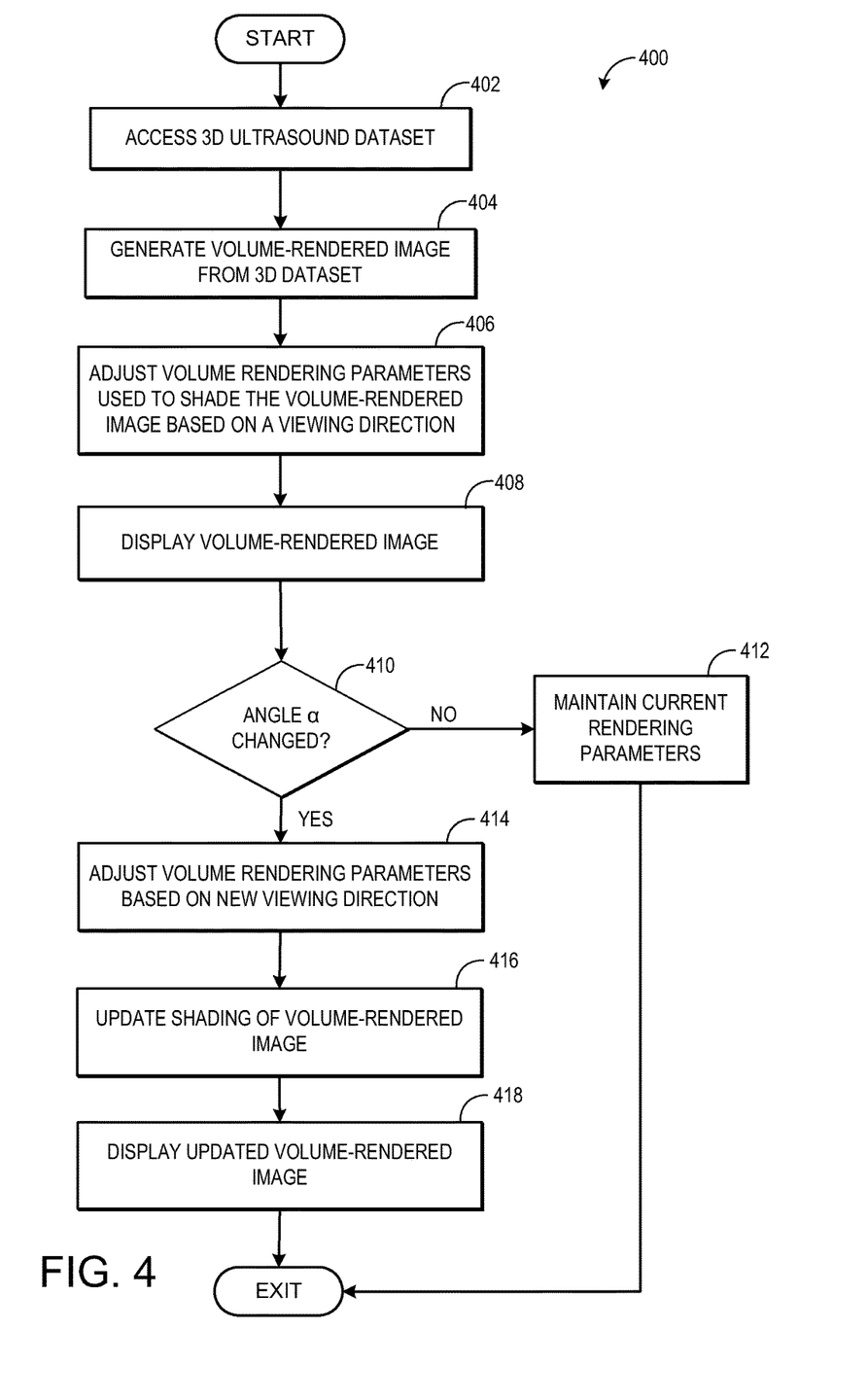
FIG. 4 is a flow chart of a method for generating a volume-rendered image based on a viewing direction according to an embodiment.

FIG. 4 is a flow chart of a method 400 in accordance with an embodiment. According to exemplary embodiments, the method 400 may be performed with the system 100 shown in FIG. 1. The technical effect of the method 400 is the display of a volume-rendered image that is shaded and/or shadowed based on a viewing direction of the volume-rendered image relative to a probe axis of a transducer probe (as shown in FIG. 3) used to acquire the three-dimensional (3D) data. FIG. 4 will be described according to an exemplary embodiment where the method 400 is performed with the ultrasound imaging system 100 shown in FIG. 1. However, according to other embodiments, the method 400 may also be performed with other ultrasound imaging systems or with different medical imaging devices. Additionally, according to other embodiments, the method 400 may be performed by a workstation that has access to 3D ultrasound data that was acquired by a separate ultrasound imaging system.

An ultrasound imaging system acquires a 3D medical imaging dataset (e.g., 3D ultrasound dataset) with a transducer probe and stores the medical imaging dataset in the memory of the system (such as memory 120 shown in FIG. 1). The transducer probe is positioned on an object surface.

Method 400 begins at step 402, where the processor of the ultrasound imaging system (such as processor 116 shown in FIG. 1) accesses a 3D ultrasound imaging dataset from a memory, such as the memory 120 shown in FIG. 1. In another embodiment, the 3D ultrasound data may be accessed in real-time as the data is acquired by the ultrasound probe (e.g., such as probe 105 shown in FIG. 1). The 3D ultrasound dataset may include voxel data where each voxel is assigned a value and an opacity. The value and opacity may correspond to the intensity of the voxel. At 404, the processor generates a volume-rendered image from the 3D ultrasound imaging dataset. According to an embodiment, the processor may generate the volume-rendered image according to one of the techniques previously described with respect to FIG. 2. As part of the generation of the volume-rendered image during 404, the processor determines (e.g., calculates) the shading for the volume-rendered image. As described hereinabove with respect to FIGS. 2-3, the shading of the volume-rendered image may include calculating how light from one or more distinct light sources would interact with the structures represented in the volume-rendered image. The volume rendering algorithm controlling the shading may calculate how the light would reflect, refract, and diffuse based on intensities, opacities, and gradients in the 3D ultrasound imaging dataset. The intensities, opacities, and gradients in the 3D ultrasound imaging dataset may correspond with tissues, organs, and structures in the volume-of-interest from which the 3D ultrasound dataset was acquired. As one example, at 404, the processor uses the light from the one or more light sources in order to calculate the amount of light along each of the rays used to generate the volume-rendered image. The positions, orientations, and other parameters associated with the one or more lights sources will therefore directly affect the appearance of the volume-rendered image. In addition, the light source(s) may be used to calculate shading with respect to surfaces represented in the volume-rendered image. In one example, the shading may be adjusted based on a position of the light source relative to the volume-rendered image.

As described above, shading and/or shadowing the volume-rendered image may include applying one or more of depth coloring, direct lighting, indirect lighting, ambient lighting, specular and diffuse reflections, and HDR processing to the volume-rendered image. Further, applying shading and/or shadowing to the volume-rendered image at 404 may include calculating shading of the volume-rendered image based on one or more volume-rendering shading parameters. As one example, the one or more volume-rendering shading and shadowing parameters may include a light reflection parameter (e.g., such as a specular reflection parameter) and a light attenuation parameter, where the light reflection parameter determines an amount (e.g., strength) of shading and the light attenuation parameter determines an amount (e.g., strength) of shadowing applied to the volume-rendered image.

At 406, the method includes adjusting one or more of the volume-rendering shading and shadowing parameters used to shade and shadow the volume-rendered image based on a viewing direction of the volume-rendered image relative to the probe axis of the transducer probe. As described above with reference to FIG. 3, the viewing direction may be a direction in which a viewer (e.g., user) views the volume-rendered image. For example, the viewer may view the volume-rendered image from a radial direction (e.g., a direction parallel to the transducer probe axis, as applied to the tissue represented by the volume-rendered image), a lateral direction (e.g., a direction perpendicular to the transducer probe axis), an elevation direction, or some other direction in between these directions. An angle, $\alpha$, is defined between the transducer probe axis (e.g., central axis of the transducer probe normal to the transducer surface, as described above with regard to FIG. 3) and the viewing direction, as shown in FIG. 3. The angle $\alpha$ is then input into a weighting function for angle dependency, such as equation 1 described above with reference to FIG. 3. The output of the weighting function is then applied to the volume rendering algorithm to adjust the volume rendering parameters. For example, the output of the weighting function may be applied to the one or more volume rendering parameters used to shade the volume-rendered image, such as the light reflection parameter and the light attenuation parameter (e.g., opacity). As another example, the output of the weight function may be applied to the light attenuation parameter (e.g., opacity) used to shade the volume-rendered image. As a result, the shading and shadowing of the volume-rendered image is adjusted based on the angle $\alpha$.

At 408, the processor displays the angle-dependent, shaded and shadowed volume-rendered image on a display device (such as display device 118) of the ultrasound imaging system. At 410, the processor determines if the angle $\alpha$ has changed. For example, the processor may receive a signal from the user interface, indicating that a user has moved (e.g., rotated) the volume-rendered image, thereby changing the viewing direction of the volume-rendered image, and the angle $\alpha$ has changed. For example, the user may rotate the volume-rendered image from the radial direction to the lateral direction in order to view the image from the side vs. a top view while the probe axis remains the same. As a result, the angle $\alpha$ increases. In another example, during an acquisition event where a user may adjust a position of the transducer probe, the probe axis may change, thereby changing the angle $\alpha$. Thus, the angle $\alpha$ may change responsive to the viewing direction and/or the probe axis changing.

If the processor has not received a signal indicating that the angle $\alpha$ has changed, the method continues to 412 to maintain the current volume-rendering shading parameters used to shade the volume-rendered image. Alternatively, if the angle $\alpha$ has changed, the method continues to 414 where the processor adjusts the volume-rendering shading and shadowing parameters based on the newly received angle $\alpha$ (which is different than the original angle). The method at 414 may follow a similar method to that of 406. For example, the processor may update the weighting term based on the new angle $\alpha$. The processor may then apply the updated weighting term to the one or more volume-rendering shading parameters (e.g., the light reflection parameter and the light attenuation parameter) and shadowing parameters (e.g. the light attenuation parameter). At 416, the processor updates the shading of the volume-rendered image based on the adjusted shading and shadowing volume rendering parameters. In one example, if the new angle $\alpha$ is greater than the previous angle $\alpha$ (e.g., the viewing direction has moved further from the radial direction and the probe axis), the amount of shading and shadowing of the volume-rendered image is reduced from the volume-rendered image displayed at 408. Even if the probe axis stays the same, if the viewing direction moves, then the angle α changes and the shading and shadowing are updated at 416. At 418, the processor displays (e.g., via a display device) the updated volume-rendered image having the updated shading and shadowing. In some examples, the adjusting and updating at 414 and 416 may occur while a user is acquiring 3D ultrasound data with the transducer probe and the volume-rendered images may be shaded, shadowed, and updated in real-time.

In different embodiments, only one of or both of shading and shadowing may be used to generate the volume-rendered image. Thus, method 400 may include applying and adjusting one or both of shading and shadowing to the volume-rendered image. As one example, only shading and not shadowing may be applied to and used to generate the volume-rendered image. As such, when the viewing angle changes, only the shading parameters may be adjusted for the volume-rendered image. In another example, only shadowing and not shading may be applied to the volume-rendered image. Thus, when the viewing angle changes, only the shadowing parameters may be adjusted for generating the updated volume-rendered image. In yet another example, both shading and shadowing may be applied to generate the volume-rendered image. The determination of whether to apply shading, shadowing, or both, to the volume-rendered image may be based on different conditions (e.g., such as the type of tissue acquired, the imaging system properties, the preference of the user, the type of diagnostic being performed based on the generated volume-rendered image, the viewing angle, etc.). Thus, there may be different conditions for applying shading, shadowing, or both to the volume-rendered image. In one example, a user may select which of the shading, shadowing, or both, are applied when generating the volume-rendered image. In this way, the shading and shadowing of the volume-rendered image is independently enabled by the user. Further, different amount of shading and shadowing may be applied to the same image. For example, a user may select to apply a greater amount of shading than shadowing to the volume-rendered image. In this way, the degree of each of the shading and shadowing may be selected. Further still, different parts (e.g., regions) of a single volume-rendered image or different images in a time sequence of an acquisition event, may be shaded and shadowed differently (e.g. different amount of each of shading and shadowing may be applied, or only one or the another may be applied). In all cases, both the shading and shadowing are created and updated based on the same angle between the probe axis of the transducer probe and the viewing direction of the volume rendered image (e.g., a, as described above). For example, when both shading and shadowing are used to generate the volume-rendered image, both the shading and shadowing are based on the same angle between the probe axis and the viewing direction.

In this way, a volume-rendered image generated from a three-dimensional ultrasound dataset may be shaded and/or shadowed based on an angle between a probe axis of a transducer probe and a viewing direction of the volume-rendered image. For example, one or more volume-rendering shading and shadowing parameters used to calculate the shading and/or shadowing of the volume-rendered image may be adjusted based on the determined angle between the probe axis and the viewing direction. As the angle increases, an amount of shading and/or shadowing applied to the volume-rendered image may be reduced, thereby increasing a quality of the image resolution at different viewing directions. Since the resolution of the image is anisotropic, adjusting the shading and/or shadowing of the volume-rendered based on the angle between the probe axis and the viewing direction reduces the noise and smoothens the volume rendered image. As a result, more accurate medical diagnosis may be made from any viewing direction of the volume-rendered image.

As one embodiment, a method for ultrasound imaging comprises generating a volume-rendered image with shading and shadowing from a three-dimensional ultrasound dataset, the shading and shadowing based on an angle between a probe axis of a transducer probe used to acquire the three-dimensional ultrasound dataset and a viewing direction of the volume-rendered image. As one example, the shading and shadowing for the volume-rendered image are determined based on a light source and one or more volume-rendering shading and shadowing parameters, where the one or more volume-rendering shading and shadowing parameters are adjusted based on the angle. The method may further comprise adjusting the one or more volume-rendering shading and shadowing parameters by multiplying the one or more volume-rendering shading and shadowing parameters by a weighting function, wherein the weighting function is a function of the angle, and wherein the weighting function decreases an amount of shading and shadowing of the volume-rendered image as the angle increases. In one example, the weighting function includes an angle dependency term. In another example, the one or more volume-rendering shading and shadowing parameters includes a light attenuation parameter that determines a shade and shadow strength for the volume-rendered image and a light reflection parameter that determines an intensity of the reflected light. The method may further comprise determining an amount of shadowing and shading of the volume-rendered image based on the adjusted one or more volume-rendering shading and shadowing parameters and reducing the amount of shadowing and shading as the angle increases. The method may additionally comprise displaying the volume-rendered image. As another example, in response to a change in the angle, the method may include updating the shading and shadowing based on the change in the angle and displaying the volume-rendered image with the updated shading and shadowing. Additionally, the probe axis is a central axis of the transducer probe which is positioned normal to a plane tangent to a surface formed by transducer elements of the transducer probe.

As another embodiment, a method for ultrasound imaging comprises generating a volume-rendered image with a first shading and a first shadowing from a three-dimensional ultrasound dataset, the first shading and the first shadowing based on an angle between a probe axis of a transducer probe used to acquire the three-dimensional ultrasound dataset and a viewing direction of the volume-rendered image; displaying the generated volume-rendered image; and in response to a change in the angle, updating the volume-rendered image with a second shading and a second shadowing, different than the first, the second shading and the second shadowing based on the change in the angle, and displaying the updated volume-rendered image. In one example, generating the volume-rendered image with the first shading and the first shadowing includes calculating the first shading and the first shadowing for the volume-rendered image based on one or more volume-rendering shading parameters, where the one or more volume-rendering shading and shadowing parameters are adjusted based on the angle. The method may further comprise adjusting the one or more volume-rendering shading and shadowing parameters by multiplying the one or more volume-rendering shading and shadowing parameters by a weighting function, where the weighting function is a function of the angle and includes an angle dependency term. Further, as one example, the one or more volume-rendering shading and shadowing parameters that are adjusted based on the angle include a light reflection parameter and a light attenuation parameter. As another example, updating the volume-rendered image with the second shading and the second shadowing includes calculating the second shading and the second shadowing based on one or more volume-rendering shading and shadowing parameters, where the one or more volume-rendering shading and shadowing parameters are adjusted based on the change in the angle. The method may further comprise, in response to the angle increasing, adjusting the one or more volume-rendering shading and shadowing parameters by a greater amount than for the first shading and the first shadowing and decreasing an amount of shading and shadowing applied to the volume-rendered image. In another example, the method may further comprise, in response to the angle decreasing, adjusting the one or more volume-rendering shading and shadowing parameters by a smaller amount than for the first shading and the first shadowing and increasing an amount of shading and shadowing applied to the volume-rendered image. Additionally, as one example, resolution of the three-dimensional ultrasound dataset is anisotropic.

As yet another embodiment, an ultrasound imaging system having an anisotropic point spread function, comprises: a transducer probe adapted to scan a volume of interest; a display device; a user interface; and a processor in electronic communication with the transducer probe, display device, and user interface. The processor is configured to: generate a volume-rendered image from three-dimensional ultrasound data acquired with the transducer probe; apply one or more shading and shadowing parameters to the volume-rendered image; adjust the one or more shading and shadowing parameters based on an angle between a probe axis of the transducer probe and a viewing direction of the volume-rendered image; and display the volume-rendered image on the display device. As one example, the processor is further configured to adjust the one or more shading and shadowing parameters by multiplying the one or more shading and shadowing parameters by a weighting function, where the weighting function includes an angle dependency term and is a function of the angle. Additionally, the processor may be further configured to: receive a change in the viewing direction from the user interface; determine the angle based on the change in the viewing direction and a current probe axis; and if the angle has changed, adjust the one or more shading and shadowing parameters based on the changed angle to update the shading and shadowing of the volume-rendered image and display the volume-rendered image on the display device with the updated shading.

As used herein, an element or step recited in the singular and proceeded with the word "a" or "an" should be understood as not excluding plural of said elements or steps, unless such exclusion is explicitly stated. Furthermore, references to "one embodiment" of the present invention are not intended to be interpreted as excluding the existence of additional embodiments that also incorporate the recited features. Moreover, unless explicitly stated to the contrary, embodiments "comprising," "including," or "having" an element or a plurality of elements having a particular property may include additional such elements not having that property. The terms "including" and "in which" are used as the plain-language equivalents of the respective terms "comprising" and "wherein." Moreover, the terms "first," "second," and "third," etc. are used merely as labels, and are not intended to impose numerical requirements or a particular positional order on their objects.

The control methods and routines disclosed herein may be stored as executable instructions in non-transitory memory and may be carried out by a processor of an imaging system in combination with the various hardware of the imaging system, such as a transducer probe, user interface, and display.

This written description uses examples to disclose the invention, including the best mode, and also to enable a person of ordinary skill in the relevant art to practice the invention, including making and using any devices or systems and performing any incorporated methods. The patentable scope of the invention is defined by the claims, and may include other examples that occur to those of ordinary skill in the art. Such other examples are intended to be within the scope of the claims if they have structural elements that do not differ from the literal language of the claims, or if they include equivalent structural elements with insubstantial differences from the literal languages of the claims.

The invention claimed is:

1. A method for ultrasound imaging, comprising:
generating a volume-rendered image with at least one of shading and shadowing from a three-dimensional ultrasound dataset, the shading and shadowing based on an angle between a probe axis of a transducer probe used to acquire the three-dimensional ultrasound dataset and a viewing direction of the volume-rendered image.

2. The method of claim 1, wherein the at least one of shading and shadowing for the volume-rendered image are determined based on a light source and one or more volume-rendering shading and shadowing parameters, where the one or more volume-rendering shading and shadowing parameters are adjusted based on the angle.

3. The method of claim 2, further comprising adjusting the one or more volume-rendering shading and shadowing parameters by multiplying the one or more volume-rendering shading and shadowing parameters by a weighting function, wherein the weighting function is a function of the angle, and wherein the weighting function decreases an amount of shading and shadowing of the volume-rendered image as the angle increases.

4. The method of claim 3, wherein the weighting function includes an angle dependency term.

5. The method of claim 3, wherein the one or more volume-rendering shading and shadowing parameters includes a light attenuation parameter that determines a shadow strength for the volume-rendered image and a reflection parameter that determines an intensity of the reflected light.

6. The method of claim 2, further comprising determining an amount of the at least one of the shadowing and shading of the volume-rendered image based on the adjusted one or more volume-rendering shading and shadowing parameters and further comprising reducing the amount of the at least one of the shadowing and shading as the angle increases.

7. The method of claim 1, further comprising generating the volume-rendered image with both shading and shadowing and displaying the volume-rendered image, wherein the shading and shadowing includes surface light attenuation and surface light reflectivity in the displayed image.

8. The method of claim 7, further comprising in response to a change in the angle, updating the shading and shadowing based on the change in the angle and displaying the volume-rendered image with the updated shading and shadowing.

9. The method of claim 1, wherein the probe axis is a central axis of the transducer probe which is positioned normal to a plane tangent to a surface formed by transducer elements of the transducer probe.

10. A method for ultrasound imaging, comprising:
generating a volume-rendered image with at least one of a first shading and a first shadowing from a three-dimensional ultrasound dataset, the at least one of the first shading and the first shadowing based on an angle between a probe axis of a transducer probe used to acquire the three-dimensional ultrasound dataset and a viewing direction of the volume-rendered image;
displaying the generated volume-rendered image; and
in response to a change in the angle, updating the volume-rendered image with at least one of a second shading and a second shadowing, different than the first, the at least one of the second shading and the second shadowing based on the change in the angle, and displaying the updated volume-rendered image.

11. The method of claim 10, wherein generating the volume-rendered image with the at least one of the first shading and the first shadowing includes calculating the at least one of the first shading and the first shadowing for the volume-rendered image based on one or more volume-rendering shading and shadowing parameters, where the one or more volume-rendering shading and shadowing parameters are adjusted based on the angle.

12. The method of claim 11, further comprising adjusting the one or more volume-rendering shading and shadowing parameters by multiplying the one or more volume-rendering shading and shadowing parameters by a weighting function, wherein the weighting function is a function of the angle and includes an angle dependency term.

13. The method of claim 11, wherein the one or more volume-rendering shading and shadowing parameters that are adjusted based on the angle include one or more of a light reflection parameter and a light attenuation parameter.

14. The method of claim 10, wherein updating the volume-rendered image with the at least one of the second shading and the second shadowing includes calculating at least one of the second shading and the second shadowing based on one or more volume-rendering shading parameters, where the one or more volume-rendering shading and shadowing parameters are adjusted based on the change in the angle.

15. The method of claim 14, further comprising:
in response to the angle increasing, adjusting the one or more volume-rendering shading and shadowing parameters by a greater amount than for the at least one of the first shading and first shadowing and decreasing an amount of shading and shadowing applied to the volume-rendered image; and
in response to the angle decreasing, adjusting the one or more volume-rendering shading and shadowing parameters by a smaller amount than for the at least one of the first shading and the first shadowing and increasing an amount of shading and shadowing applied to the volume-rendered image.

16. The method of claim 1, further comprising generating the volume-rendered image with both the first shading and the first shadowing, where both the first shading and first shadowing are based on the angle, and in response to the change in the angle, updating the volume-rendered image with both the second shading and the second shadowing, where both the second shading and the second shadowing is based on the change in the angle.

17. The method of claim 10, wherein the three-dimensional ultrasound dataset is anisotropic and wherein the shading includes light reflection and the shadowing includes light attenuation.

18. An ultrasound imaging system having an anisotropic point spread function, comprising:
a transducer probe adapted to scan a volume of interest;
a display device;
a user interface; and
a processor in electronic communication with the transducer probe, display device, and user interface, where the processor is configured to:
generate a volume-rendered image from three-dimensional ultrasound data acquired with the transducer probe;
apply one or more shading and shadowing parameters to the volume-rendered image;
adjust the one or more shading and shadowing parameters based on an angle between a probe axis of the transducer probe and a viewing direction of the volume-rendered image; and
display the volume-rendered image on the display device.

19. The system of claim 18, wherein the processor is further configured to adjust the one or more shading and shadowing parameters by multiplying the one or more shading and shadowing parameters by a weighting function, where the weighting function includes an angle dependency term and is a function of the angle.

20. The system of claim 18, wherein the processor is further configured to:
receive a change in the viewing direction from the user interface;
determine the angle based on the change in the viewing direction and a current probe axis; and
if the angle has changed, adjust the one or more shading and shadowing parameters based on the changed angle to update the shading and shadowing of the volume-rendered image and display the volume-rendered image on the display device with the updated shading and shadowing.

* * * * *